United States Patent [19]

Hanson

[11] Patent Number: 4,883,070
[45] Date of Patent: Nov. 28, 1989

[54] ENDOCARDIAL PACING LEAD

[76] Inventor: Ralph E. Hanson, Pace Medical, Inc., 391 Totten Pond Rd., Waltham, Mass. 02154

[21] Appl. No.: 163,367

[22] Filed: Mar. 2, 1988

[51] Int. Cl.⁴ .............................................. A61N 1/05
[52] U.S. Cl. .................................... 128/785; 128/786; 128/419 P
[58] Field of Search ................................ 128/784–786, 128/419 P, 642

[56] References Cited

U.S. PATENT DOCUMENTS

| 4,236,529 | 12/1980 | Little | 128/785 |
| 4,301,815 | 11/1981 | Doring | 128/785 |
| 4,402,328 | 9/1983 | Doring | 128/785 |
| 4,564,023 | 1/1986 | Hess | 128/785 |

FOREIGN PATENT DOCUMENTS

| 3146182 | 6/1983 | Fed. Rep. of Germany | 128/419 P |
| 3415410 | 10/1984 | Fed. Rep. of Germany | 128/419 P |

Primary Examiner—Lee S. Cohen
Attorney, Agent, or Firm—Nutter, McClennen & Fish

[57] ABSTRACT

An endocardial pacing lead has a fixator in the form of a thin, deeply scalloped, flexible and resilient skirt that flares out from the body of the lead away from the contact tip thereof. The skirt defines a continuous frustoconical skirt portion adjacent to the body and a plurality of elongated, relatively wide, thin leaves extending from the free edge of the skirt that constitute flexible resilient extensions of the skirt.

10 Claims, 1 Drawing Sheet

ENDOCARDIAL PACING LEAD

This invention relates to an endocardial pacing lead or sensing electrode. It relates more particularly to a lead or electrode for establishing an electrical connection between heart tissue and a pacemaker or other heart management o monitoring apparatus that applies electrical signals to or receives them from the heart.

BACKGROUND OF THE INVENTION

A pacemaker is an electrical device that provides precisely timed electrical signals to stimulate the heart. A pacing lead or electrode is a flexible insulated conductor terminated by a rigid body having an exposed contact point or tip which conducts the signals from the pacemaker to an appropriate location in the heart. While sometimes the lead is sutured into the heart muscle, more often it is inserted into the right ventricle or right atrium by the so-called transvenous approach. The same type of lead is used to conduct signals produced by the heart to various sensing and monitoring instruments.

Usually such pacing and sensing leads have fixation means near the tip of the device to maintain the tip in electrical contact with heart tissue adjacent to the tip. Such means have included fine wire hooks mounted adjacent to the tip which spring out into adjacent tissue or trabeculations within the heart. The hooks do achieve fixation. However, when it becomes necessary for one reason or another, to remove the lead, they are difficult to dislodge without causing at least some damage to heart tissue.

To avoid that problem, in lieu of hooks, more recent leads and electrodes of this general type are formed with flexible resilient plastic or silicone rubber projections which engage the trabeculations and cooperate with tissue ingrowth to maintain the lead tip in intimate electrical contact with stimulatable (viable) heart tissue. For example, U.S. Pat. No. 3,719,190 discloses a lead with a cone or parachute of resilient insulating material which extends out behind the lead tip. The cone is collapsible so that it can be passed through an introducing device or the vein itself when the electrode is being inserted. Also being resilient, it resumes its original shape upon leaving the introducing device or entering larger diameter veins so that after the lead tip is properly positioned in one of the heart cavities, the cone edge engages adjacent trabeculations and usually holds the lead in place until tissue ingrowth firmly anchors the lead. This type of lead can be withdrawn from the patient if that becomes necessary by pulling on the insulated conductor lead. This usually causes the parachute to invert and release from the tissue ingrowth and present a tapered face in the withdrawal direction so that it can be pulled back through the vein of introduction and/or the introducing device.

This prior lead is disadvantaged in that the cone or parachute, when collapsed, still has a relatively large cross section so that a relatively large introducing device or vein is required in order to insert that lead into the patient. This is undesirable because it requires a correspondingly large incision in the patent. Also, when the lead tip is positioned within the heart, the circular edge of the parachute does not always engage or grab the adjacent heart tissue or trabeculations firmly enough to fix the position of the tip until there has been sufficient tissue ingrowth to anchor the lead. Furthermore, even though that lead is designed to be removable, in practice, the parachute exhibits sufficient resistance to inversion as to make it relatively difficult to withdraw the lead back out through the introducing device or catheter.

U.S. Pat. Nos. 3,902,501 and 3,939,843 disclose endocardial leads with three or four outwardly-rearwardly extending pliant uniformly cylindrical tines for holding the leads in place within the heart. While these tines provide better retention of the lead then the aforesaid parachute, they also have certain drawbacks. More particularly, the tines, which vary in length from 2 to 5 mm, have very small cross sections, e.g. 1 to 2 mm, so that there is very little material at the roots of the tines where they join the lead body. In some cases, a pulling force of as little as 1½ pounds is enough to separate a tine or a portion thereof from the remainder of the lead. A pulling force of this order can easily be experienced when it becomes necessary to reposition the lead by pulling or manipulating the lead's insulated conductor after the lead has become dislodged due to heart wall movements.

Another occasion for such tine separation is when the lead is being inserted into the heart across the tricuspid valve. If the tines are of the type which are relatively long and stiff, they can become caught in the valve and such separation may occur during efforts to free the lead, not infrequently causing inversions and/or damage to valve leaflets in the process. Tine separation can also occur when the lead is being retracted through the introducing device. The introducing device is a special hollow catheter that is inserted into the patient's vein, commonly the subclavian vein, in order to facilitate the insertion of and to guide the lead and to eliminate the need for the more time consuming venous cut down. The distal or inner end of this introducing device has a small diameter and a thin wall so that it presents a relatively stiff and sharp edge. When a tined lead is being inserted into a patient, its tines are pressed against the lead body by the wall of the introducing device. However, as soon as the tines pass through the distal or inner end of the introducing device, they spring out to their normal extended positions. Sometimes, however, when threading the lead along the venous course to, or during repositioning in the heart, it becomes necessary to pull the lead body back into the introducing device. In the process, the fine rearwardly angled tines are drawn against the stiff sharp edge of the introducing device causing cuts in the tines. In extreme cases, the cutting can be sufficiently severe to greatly weaken the tines or even to separate them from the remainder of the lead. This same cutting problem also arises when the lead is withdrawn from a patient after it is no longer needed. Suffice it to say, the presence of a loose tine or segment thereof in a patient's venous system may constitute a life-threatening hazard to the patient.

A tined lead is disadvantaged also in that, like the parachute electrode, it requires an introducing device with a relatively large lumen. In other words, even when the tines are folded back against the lead body, the overall body cross section is still relatively large. For example, a typical lead with either long or short tines requires a No. 9 introducing device as measured on the French Catheter Scale.

Also the tines on such a lead, being tiny cylinders that project out from the lead body have no preferred direction of deflection or bending. Thus, when the lead is being inserted through an introducing device or vein, the tines may not lie symmetrically about the axis of the lead body. In other words, they may extend in different directions or be wrapped to a greater or lesser degree one way or another about that body. When the tines are relatively long, one tine may even overlap another tine thereby increasing the effective cross section of the lead. Resultantly, the lead may not feed through the introducing device and vein particularly smoothly and uniformly thereby making it more difficult for the surgeon to insert the lead into a patient. Similarly, when the lead has to be withdrawn, the tines do not necessarily simply invert. Again, they may extend and wrap in different directions about the lead body making it more difficult if not impossible to withdraw the lead through the patient's vein. Such random deflection and wrapping also increases localized stresses on the individual tines increasing the possibility of a tine or a portion thereof breaking away from the body of the lead.

SUMMARY OF THE INVENTION

Accordingly, it is an object of the present invention to provide an improved endocardial pacing lead or sensing electrode.

Another object of the invention is to provide such a lead which achieves superior fixation of the lead body within the heart or other organ.

A further object of the invention is to provide a pacing lead which can be inserted into and withdrawn from a patient's vein or artery using a relatively small introducing device.

Yet another object of the invention is to provide a pacing lead which facilitates smooth and easy introduction of the lead into and its withdrawal from a patient.

Another object of the invention is to provide a pacing lead of this type whose body is not prone to being caught or hung up within the cavities of the heart.

A further object of the invention is to provide an endocardial pacing lead which can be inserted into and removed from a patient's heart cavities with greater safety for the patient and with minimal difficulty for the surgeon.

Other objects will, in part, be obvious and will, in part, appear hereinafter. The invention accordingly comprises the features of construction, combination of elements and arrangement of parts which will be exemplified in the construction hereinafter set forth, and the scope of the invention will be indicated in the claims.

Briefly, the pacing lead comprises a flexible insulated electrical conductor. The proximal end of the conductor is terminated by a conventional male or female electrical connector adapted to connect to the input and/or output of electrical apparatus for monitoring or managing a patient's heart by sending and/or receiving electrical signals to or from the heart, e.g. a pacemaker. The opposite or distal end of the insulated conductor is terminated by a body having an exposed electrically conductive contact point or tip capable of conducting electrical current between the electrical apparatus, via the insulated conductor, and heart tissue. As usual, fixation means are provided on the lead body to anchor the body after it has been positioned at the proper location within one of the cavities of the heart. Here, however, the fixation means are distinctly different from those on prior comparable leads of this general type and they yield unique advantages not found in conventional electrodes and leads.

In the present lead structure, the fixation means comprise a flexible, resilient, deeply scalloped skirt located just behind the tip of the lead and which flares out from the lead body away from the tip. The deeply scalloped skirt thus forms a circular array of thin, flexible, resilient, tapered leaves joined by thin, flexible, resilient webs which extend out from the lead body between adjacent leaves. These tapered leaves, which have curved cross sections and are quite thin, are able to fold flush against the lead body so that the overall diameter of the lead is relatively small. Therefore, the lead can be inserted through a relatively small introducing device which requires only a relatively small incision in the vein. Also, the flat curved leaves have essentially only a single degree of freedom toward and away from the lead body; they will not tend to bend or deflect laterally or circumferentially. This means that in their folded or inverted folded positions, the leaves always lie flush against the lead body; they never become skewed or overlap. Accordingly, when a surgeon is inserting or removing the lead, movement of the lead along the introducing device and vein will be smooth and regular thereby facilitating the insertion and removal processes.

Also, when the lead is being inserted into or being withdrawn from the heart, the flat tapered leaves are not prone to being caught in the tricuspid valve. In response to the surgeon's manipulation of the lead, the leaves are able to fold or invert as needed to disengage from the obstructing tissue, returning to their natural orientations as soon as they are free.

When my lead is properly positioned within a heat cavity, the thin, tapered and curved or bowed leaves provide very effective fixation to adjacent tissue. Each leaf is, in effect, a cantilevered beam with a curved cross section so that even though the leaf itself is quite thin, it still has appreciable stiffness. Also the thin, doubly curved edges at the ends of the leaves are particularly effective in grabbing and anchoring to adjacent tissue or trabeculations.

It is important to note also that the leaves themselves are quite strong with most of the mass or material of the leaves being located near their roots where most of the stresses imposed on the leaves are likely to be concentrated. In other words, unlike tined electrodes whose small diameter uniformly cylindrical tines have very little material or mass at the joints between the tines and the lead body, the fixation leaves on my electrode are quite wide at their bases or roots and those bases are all interconnected by way of the flexible resilient webs which extend out from the lead body and join adjacent leaves.

In other words, the fixation means on this lead may be considered as having two parts that combine and cooperate to form an integral whole. The first part is a flexible, resilient, thin frustoconical skirt that flares out from the lead body. This skirt extends all around the body so that it has a strong overall connection to the body. The second part is the circular array of thin tapered and curved, flexible and resilient leaves which are integral to and extend out from the circular edge of that skirt which edge is spaced away from the lead body. The edge boundaries between the skirt and leaves are shaped to provide smooth, gently inwardly curved transitions between the leaves all around the lead. This construction gives the overall fixation means a stiffness gradient along its length, with the bending or flexing movements thereof being limited to a single degree of freedom toward and away from the lead body.

That is, each leaf is most flexible and most capable of inversion near its free end where the leaf is narrowest.

The leaf becomes progressively stiffer towards its root or base where it connects to the frustoconical skirt that continues into the body of the lead. Thus, each leaf is more prone or more susceptible to flexure or inversion at or near its tip than at or near its root. Accordingly, when it becomes necessary to manipulate the lead's insulated conductor in order to reposition or withdraw the lead body, the leaves tend to flex first closer to their ends. In response to stronger pulling or flexing forces, the leaves bend or invert closer to their roots. However, being wider at those locations, they are better able to withstand the larger stresses which impact those locations when large pulling, bending or flexing forces are required in order to reposition or dislodge the lead. The frustoconical skirts connecting the roots of those leaves to the body of the electrode will also fold or invert as necessary to effect release from surrounding or obstructing tissue. However, being a closed ring of sheet material with a continuous connection to the body of the lead, the skirt is well able to tolerate even relatively large stresses caused by folding or inversion even though the web joins the lead body at a relative small acute angle.

Thus, when the surgeon pushes, pulls or otherwise manipulates the lead in order to dislodge or reposition or withdraw the lead, the parts of the scalloped fixation skirt flex only to the extent necessary to free the lead body. This minimizes stresses on the skirt; it also reduces the likelihood of damage to surrounding tissue. Only those leaves flex which are required to flex in order to free the lead and even those leaves bend or fold only to the extent necessary for that purpose. The entire skirt folds or inverts only when very strong pulling or pushing forces are required to free the electrode or when the lead body is being inserted into or withdrawn from a patient. However, since the skirt has a continuous, relatively-large area boundary with the body of the lead, these forces and stresses are distributed all around the skirt which is, therefore, well able to withstand such forces.

Even when the lead is being withdrawn by pulling the lead body back through an introducing device, there is little likelihood of the fixation skirt being cut or damaged by the edge of the introducing device. That edge will be contacted by the continuous inner section of the fixation skirt so that the forces are distributed over a continuous circular area of the skirt causing the entire skirt to invert and lie against the body of the lead. Accordingly, there are little or no localized stresses imposed upon the leaves that could cause cutting, tearing or breaking away of those parts.

Another important feature of this lead is that its fixation skirt enhances tissue ingrowth after the lead body is positioned in the heart cavity so that effective anchoring of the lead over the long term is assured. This is because the deeply scalloped fixation skirt presents a very long edge at which tissue ingrowth can occur. That is, whereas with a tined electrode, tissue ingrowth can only occur around the three or four tines projecting out from the lead body, here, tissue ingrowth occurs all around the edges of the flexible leaves and around the edges of the webs extending between those leaves, as well as in the space between those parts and the body of the lead. Thus, the areas of potential ingrowth are far more extensive than is the case with tined leads or, indeed, even with those leads described at the outset fitted with parachute-type fixators. Yet, when it comes time to reposition or withdraw my lead, this can be accomplished despite such extensive ingrowth because of the aforesaid abilities of the leaves and webs to flex and fold sufficiently to release from that tissue ingrowth.

Still, with all of the advantages discussed above, the endocardial pacing lead of this invention costs no more to make than prior comparable leads of this type. Therefore, it should find wide application wherever such pacing and sensing leads are needed.

BRIEF DESCRIPTION OF THE DRAWING

For a fuller understanding of the nature and objects of the invention, reference should be had to the following detailed description taken in connection with the accompanying drawing, in which.

DESCRIPTION OF THE PREFERRED EMBODIMENT

Figure 1:
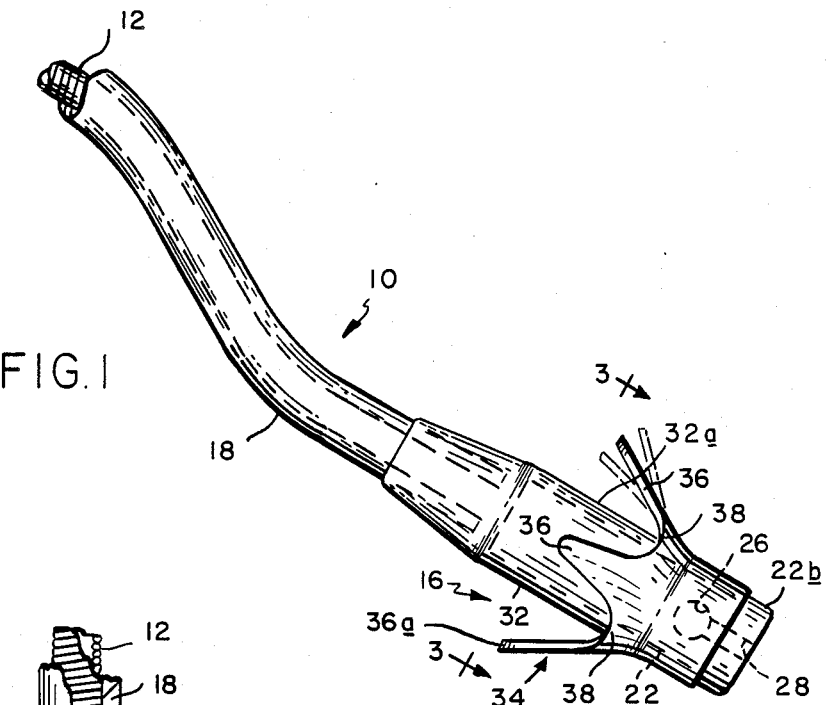
FIG. 1 is an isometric view of an endocardial pacing lead incorporating my invention.

Referring to FIG. 1 of the drawing, the endocardial pacing lead of this invention is shown generally at 10. It comprises an elongated flexible electrical conductor 12. The proximal end of the conductor 12 is terminated by a standard electrical connector (not shown) that can connect or plug into the pacemaker, monitor or other electrical apparatus with which the electrode is associated. The opposite or distal end of conductor 12 is terminated by the working end or body of the lead shown generally at 16 and the entire length of conductor 12 except at its end terminations is covered by an electrically insulated sheath or sleeve 18. Conductor 12 may consist, for example, of a length of tightly coiled stainless steel or platinum filament covered by a sheath 18 composed of PTFE or silicone rubber.

Figure 2:
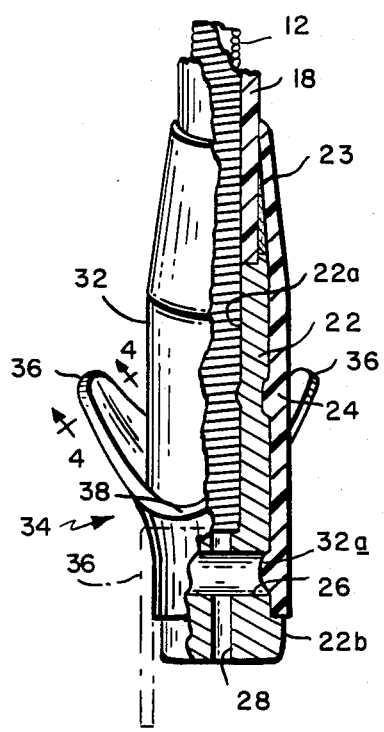
FIG. 2 is a similar view on a larger scale and with parts broken away showing portions of the FIG. 1 lead in greater detail.

Referring now to FIGS. 1 and 2, the lead's body 16 comprises a rigid conductive pin or electrode 22 made of a physiologically inert, electrically conductive material such as platinum, carbon or the like. Pin 22 has an axial bore 22a which extends from the proximal end of pin 22 almost to the distal end thereof. Bore 22a is sized to snugly receive the exposed end of conductor 12 and the proximal end of that bore is relieved to accommodate the adjacent end segment of the insulating sheath 18. The conductor is retained in bore 22a by crimping the sides of pin 22 at one or more locations as shown at 24 in FIG. 2 so that there is intimate electrical and mechanical contact between the conductor and the pin. This connection can be made even more positive and intimate both mechanically and electrically by brazing or soldering or welding those parts together. When attaching pin 22 to the end of the conductor, silicone rubber 23 can be applied to the upper or proximal end of bore 22a to assure a fluid tight joint between sheath 18 and the pin.

Pin 22 has an enlarged distal end or tip 22b which constitutes the contact point or tip of the lead. For reasons to be described later, a diametric passage 26 may be provided in the pin between the lower end of bore 22a and the electrode tip 22b. Also, a relatively small diameter axial passage 28 may extend from passage 26 to the distal end of the pin. These passages constitute weep holes that permit the escape of excess solder or other material from bore 22a when pin 22 is being connected to conductor 12. They also help to anchor to the pin the insulating sleeve 32 about to be described.

As best seen in FIG. 2, the insulating sleeve 32 completely surrounds pin 22 except at its tip 22b. The sleeve is also stretched around the end segment of conductor sheath 18 adjacent to the pin. The sleeve 32 is made of a suitable biocompatible, electrically insulating material such as PTFE or silicone rubber. It is firmly anchored to pin 22 so that the sleeve conforms closely to the pin as shown, with the electrode tip 22b projecting beyond the sleeve. Additional securement between the sleeve and the pin can be achieved by applying a suitable adhesive or bonding material (not shown) at the boundary between those two elements. Preferably also, if the pin 22 is of the type that includes the passage 26, the areas of sleeve 32 opposite the ends of that passage will flow or project somewhat into the passage thereby forming buttons 32a which insure that there will be no relative movement between sleeve 32 and pin 22.

Figure 3:
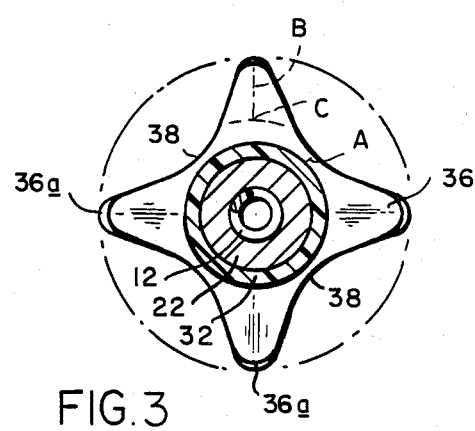
FIG. 3 is a sectional view taken along line 3—3 of FIG. 1 and slightly enlarged.

Referring to FIGS. 1 to 3, molded or otherwise formed integrally with sleeve 32 is a fixation skirt shown generally at 34 which flares out away from the sleeve at an angle in the range of 20° to 40°, the optimum angle being 30°, from a location thereon that is on the opposite side of pin passage 26 from the pin tip 22b. Skirt 34 is relatively thin, e.g. 0.4 to 0.5 mm, and its edge is deeply scalloped thereby forming a circular array of flexible resilient leaves 36 which are connected adjacent to their roots or bases by flexible resilient webs 38. In the illustrated electrode there are four each of such leaves and webs spaced 90° apart. Of course, a lead with three or five leaves in also possible. The leaves are tapered and they have rounded ends 36a. The webs 38 extend out away from sleeve 32 for a distance equal to about ⅓ the maximum length of the leaves 36. Their edges are curved so that they make smooth transitions with the edges of the adjacent leaves 36. In a typical four leaf electrode as illustrated, the distance A (FIG. 3) between the boundary of each web 38 with the sleeve 32 and the free edge (at the point of minimum height) of that web is 0.75 to 1.25 mm and the distance B between that web edge and the tip 36a of an adjacent leaf is 2.25 to 2.75 mm, with the widths C of the leaves at their bases where they join the webs being in the order of 0.75 to 1.25 mm. Typically, the webs 38 have a radius in the order of 1.2 mm.

Figure 4:
FIG. 4 is a sectional view taken along line 4—4 of FIG. 2.

As best seen in FIGS. 3 and 4, the skirt 34 as a whole is curved, as are the individual leaves 36. Furthermore, the leaves 36 are free to flex and bend individually toward and away from sleeve 32 as shown in phantom in FIG. 1. However, because they have appreciable width, they are not prone to bending or flexing in the lateral or circumferential direction.

As just noted, the leaves are curved to conform to sleeve 32. Also, they are thin and relatively narrow near their tips leaving appreciable space between adjacent leaves. Therefore, the leaves do not have to be folded longitudinally in order to nest against sleeve 32. On the other hand, the webs are not very long or high (i.e. distance A) so that the reduction in diameter of the webs when folded against sleeve 32 does not produce lengthwise folds or bulges therein. Accordingly, all leaves 36, as well as all webs 38, can be flexed or folded substantially flush against sleeve 32 without creating wrinkles or bulges in the leaves or the webs. In this compacted state, the electrode still has a relatively small overall cross section or diameter. Resultantly, it can be inserted into and withdrawn from a patient using an introducing device that has a relatively small lumen, e.g. a No. 8 introducing device as measured on the French Scale as opposed to a No. 9 for a comparably sized tined lead whose tines do not fold as compactly against the lead body. The webs 38, and the fixation skirt 34 as a whole, can also be inverted so that leaves 36 extend away from conductor 12 as shown in phantom in FIG. 2 in the event such inversion becomes necessary in order to disengage the fixation skirt from tissue or trabeculations or to withdraw the lead body 16 back through a blood vessel or the introducing device. It should be understood, however, that the normal and natural positions of the leaves and webs are as shown in solid lines in FIG. 1 and those elements tend to resume those solid line positions immediately upon removal of the forces that flexed those parts in the first place.

The curve in each leaf cross section also makes it easier to flex or bend the leaf toward the sleeve than away from the sleeve. Each leaf constitutes, in effect, a cantilevered beam which is relatively stiff even though the leaf is quite thin Still further, as best seen in FIGS. 3 and 4, the leaves 36 are tapered so that they are appreciably wider at their bases where they join webs 38 than they are at their ends or tips 36a. Consequently, they possess a stiffness gradient which makes them more prone to flexing closer to their ends than at their bases. The leaves are also resiliently foldable about their longitudinal axes. Thus, when it does become necessary to push or pull the lead body 16 past an obstruction or to reposition or withdraw the lead after appreciable tissue ingrowth has occurred around the fixation skirt 34, the leaves 36 and webs 38 will flex, bend and fold to the degrees necessary to free those parts. As the forces required for that purpose increase, the leaves 36 will flex or bend closer and closer to their bases or roots. However, being wider and stronger at those locations, they are well able to withstand the increased stresses. Finally, in the presence of relatively large repositioning or withdrawal forces, the webs 38 will fold or invert as shown in phantom in FIG. 2 to free the electrode. Still, the webs, being parts of a continuous frustoconical membrane or skirt, are well able to withstand those large forces so that there is minimal likelihood of the leaves 36, webs 38 or skirt 34 as a whole being torn or broken away from sleeve 32.

Even when the lead body 16 is pulled back through an introducing device in order to remove the lead from a patient, the force imposed on the sleeve 32 by the end of the introducing device will be distributed all around the skirt 34 at the circle of contact between the edge of the introducing device and webs 38. The skirt 34 as a whole will invert and flex to the extent necessary to allow the lead body 16 to pass through the introducing body. Even then, however, there are no localized forces or stresses applied to portions of the skirt that might promote cutting, tearing or breaking away of those parts.

The sleeve 32 and integral fixation skirt 34 can be molded or otherwise formed as a unitary part which can be shrink fitted onto pin 22. Alternatively, since the sleeve material is somewhat elastic, the sleeve can be sized so that it has to be stretched to some extent in order to accept pin 22, thereafter contracting tightly about the pin and conductor sheath 18. Additional securement can be provided by a biocompatible cement or adhesive at (not shown) the boundary between the sleeve and the pin. It is even possible to mold the sleeve and the skirt on pin 22 in situ if that is a preferred mode of fabrication. In any event, the providing of the fixation skirt 34 with all of its attendant advantages discussed above on a sensing or pacing lead can be accomplished quite easily and at no more cost than is required to fabricate prior leads of this general type which do not possess the advantages described herein.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawing, be interpreted as illustrative and not in a limiting sense.

What is claimed as new and desired to be secured by Letters Patent of the United States is:

1. An endocardial pacing lead comprising
   A. a flexible insulated electrical conductor;
   B. a rigid electrically conductive electrode member having a longitudinal axis;
   C. means for mechanically and electrically connecting one end of said member to an end of said conductor, the opposite end of said member constituting a contact tip;
   D. fixation means flaring outwardly from said member and away from said tip, said fixation means including a continuous frustoconical flexible, resilient skirt portion connected only at its smaller diameter edge to said member and invertible in the direction of said axis and a plurality of elongated, relatively thin leaves projecting from the larger diameter edge of said skirt portion at spaced apart locations therealong, said leaves constituting flexible resilient extensions of said invertible skirt portion.

2. The pacing lead defined in claim I wherein each of said leaves is generally triangular with its apex pointing away from said tip.

3. The pacing lead defined in claim 1 wherein each of said leaves has a relatively wide end at said skirt portion and a narrower opposite end.

4. The pacing lead defined in claim 3 wherein each of said leaves is stiffer at its wide end than at its opposite end.

5. The pacing lead defined in claim 1 wherein said leaves are laterally curved about different axes oriented at substantially the same acute angle with respect to the longitudinal axis of said member.

6. The pacing lead defined in claim 5 wherein said acute angle is in the range of 20 to 40 degrees.

7. The pacing lead defined in claim 1 wherein said leaves have rounded ends and smooth transitions exist between the edges of said leaves and the edge of said skirt portion so that the of said fixation means as a whole is scalloped.

8. The pacing lead defined in claim 1 including an electrically insulating sleeve surrounding said member except at said tip, and said fixation means extending out from and being integral to said sleeve.

9. The pacing lead defined in claim 8 and further including a lateral passage through said member adjacent to said tip and means projecting from the inner surface of said sleeve into said passage to mechanically interlock said sleeve and said member.

10. The pacing lead defined in claim 9 and further including an axial passage in said member extending from said lateral passage to said tip.

* * * * *